United States Patent [19]

Stevens

[11] 4,053,213

[45] Oct. 11, 1977

[54] SUPPORT FOR AN OPHTHALMIC INSTRUMENT

[75] Inventor: Donn E. Stevens, Rochester, N.Y.

[73] Assignee: Bausch & Lomb Incorporated, Rochester, N.Y.

[21] Appl. No.: 722,953

[22] Filed: Sept. 13, 1976

[51] Int. Cl.² .................... A61B 3/00; B60T 13/04
[52] U.S. Cl. .............................. 351/38; 188/72.7; 188/171
[58] Field of Search ................... 351/38; 188/171

[56] References Cited

U.S. PATENT DOCUMENTS 3,812,936  5/1974  Dane .................................. 188/171

Primary Examiner—Paul A. Sacher
Attorney, Agent, or Firm—Frank C. Parker; Bernard D. Bogdon

[57] ABSTRACT

An ophthalmic instrument support is provided for supporting a container enclosing a portion of the ophthalmic instrument. The support includes a base, movable support apparatus and control apparatus for controlling the positioning of the movable support apparatus relative to the fixed support apparatus. The movable support apparatus permits pivotal movement of the container relative to the base when activated and inactivated by control apparatus.

3 Claims, 2 Drawing Figures

SUPPORT FOR AN OPHTHALMIC INSTRUMENT

CROSS-REFERENCES TO RELATED APPLICATIONS

This application is related to an application entitled "An Ophthalmic Instrument Support" by Richard C. Mohrman, to be filed simultaneously herewith and having attorney's indicia of Mohrman-6 and a common assignee.

BACKGROUND AND SUMMARY OF THE INVENTION

For many years, optometrists, ophthalmologists and individuals engaged in eye research have used an instrument to measure the anterior corneal radius of the eye. The most commonly used instrument to make this measurement is the keratometer or ophthalmometer. In operation, it is necessary for the portion containing the optical part of the instrument to be correctly positioned relative to the eye being measured. As is readily seen, the positioning of the container portion relative to the eye must take place in three dimensions. One method used to provide this three-dimensional movement has been to elevate the container portion to approximately eye level, to rotate the container portion in an arc about an axis of rotation and move the container portion toward and away from the eye to obtain the correct alignment and focus. The apparatus used to provide this movable support employs the use of multiple screws and levers, which is very time consuming, is difficult to focus the instrument and requires expensive parts.

Recently, an ophthalmic instrument has been proposed that will elevate or lower the optical portion of the instrument relative to a supporting base by using an electric motor means controlled by a switch disposed on a control rod for activating and inactivating the electric motor. The control rod also has a switch to control the pivotal movement of the container enclosing the optical portion of the instrument by activating and inactivating a solenoid powered brake.

In the present invention, an ophthalmic instrument support apparatus is provided to support a container enclosing a portion of the instrument relative to the eye being measured. A base is used to support the movable support apparatus, which in turn is used to move the container means in a pivotal motion relative to the base. A brake is interconnected between the base and movable support apparatus to prevent pivotal movement of the movable support relative to the base. This brake includes alternatively disposed a first and a second series of plates, a solenoid with a movable core, a Vee-shaped member attached to the core with the sides of the member extending over the alternatively disposed first and second plates and a clamp member attached to the outermost series of plates and between the sides of the Vee-shaped member. A control is operably connected with the solenoid to activate and inactivate the solenoid, which permits pivotal movement of the container means when so desired.

BRIEF DESCRIPTION OF THE DRAWINGS

Objects and advantages of the invention will become apparent upon reading the following description and upon reference to the drawings, in which like reference numerals refer to like elements in their various views.

DETAILED DESCRIPTION OF THE PREFERRED EMBODIMENTS

Figure 1:
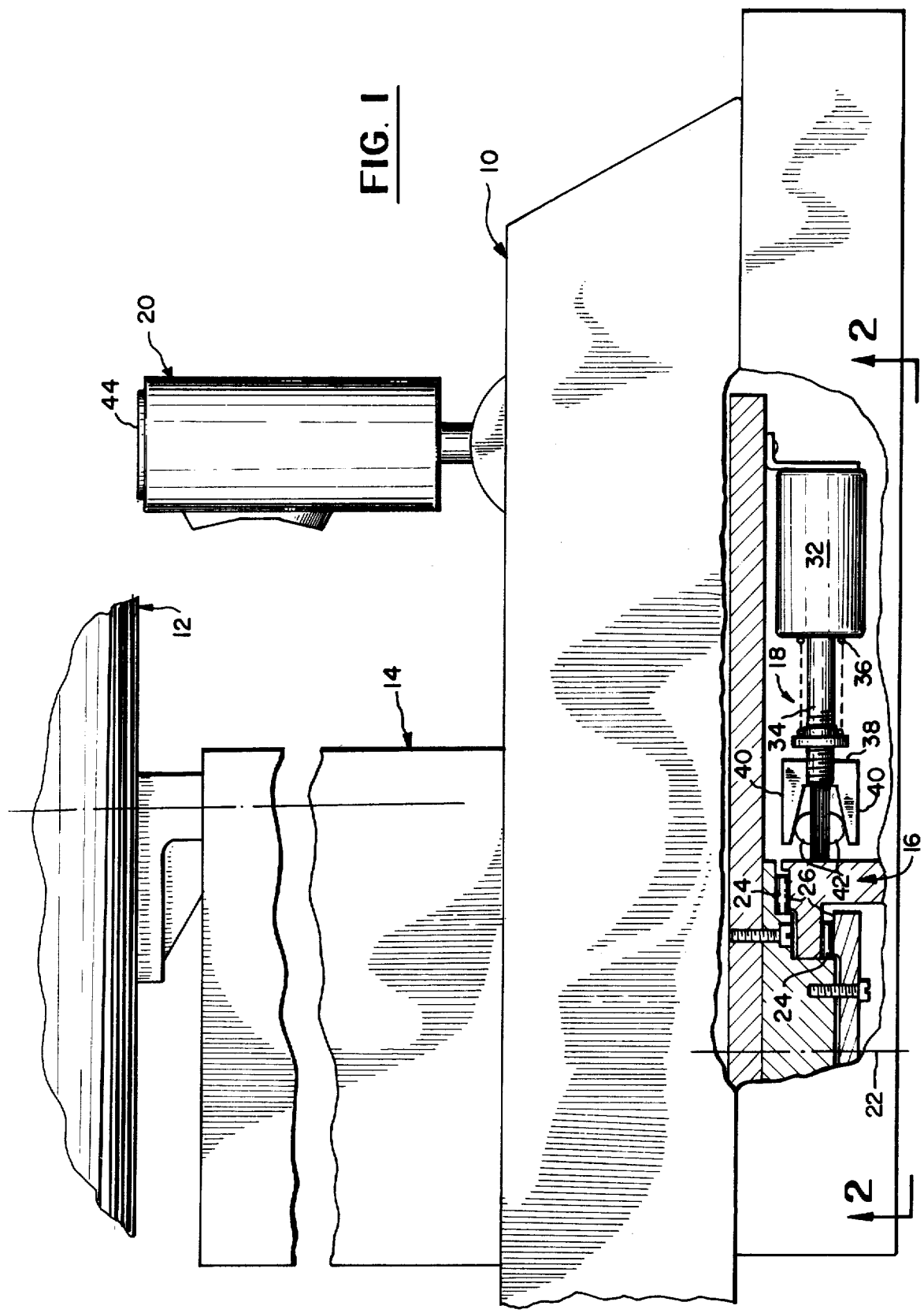
FIG. 1 is an elevational view, partly in section, of an embodiment of the present invention.

As best seen in FIG. 1, an ophthalmic instrument support apparatus 10 is generally constructed having a container 12, movable support apparatus 14, base 16, braking apparatus 18 and control apparatus 20. Normally, container 12 includes a lens system capable of providing a measurement indicating the anterior corneal radius of the eye. Such lens systems are conventional and are not considered part of the present invention.

Base 16 is used to provide support for a movable support apparatus 14, which in turn supports container 12. This configuration allows pivotal movement of movable support apparatus 14 about a pivotal axis 22 located within base 16. This is accomplished by providing roller bearings 24 in races 26, which are matingly provided between base 16 and movable support apparatus 14.

Figure 2:
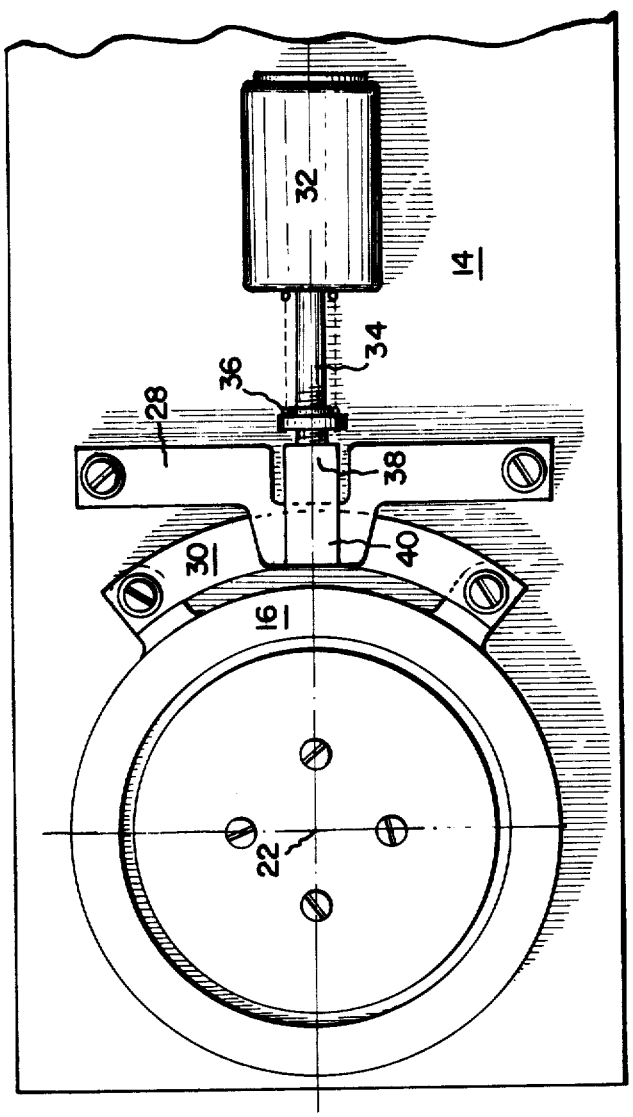
FIG. 2 is an enlarged sectional plan view, taken along lines 2—2 of the invention illustrated in FIG. 1.

As best seen in FIGS. 1 and 2, braking means 18 is provided between movable support apparatus 14 and base 16. Braking apparatus 18 basically employs the friction obtained from clamping a first series of plates 28 attached to movable support apparatus 14 to a second series of plates 30 attached to base 16. Since it is desired that the outermost plates are from first series 28, the number of plates in first series 28 is two or more and the number of plates in second series 30 is one or more. Although it is not critical to the operation of braking apparatus 18, second series of plates 30 are preferably disposed in an arc having a radius drawn from pivotal axis 22.

The clamping action is obtained through a solenoid 32 attached to movable support apparatus 14. Attached to solenoid 32 is a movable core 34, a spring 36 disposed about the movable core and a Vee-shaped member 38 attached to the end of movable core. The Vee-shaped member is constructed so that sides 40 extend over the alternatively disposed first and second series of plates, 28 and 30 respectively. A clamping member 42 is attached to the outermost plate of first series 28. Preferably, spring 36 of solenoid 32 biases Vee-shaped member 38 into a clamping position when solenoid 32 is inactivated.

An electrical switch 44 is attached to control apparatus 20. Electrical switch 44 is electrically connected to solenoid 32 for activation and activation of braking apparatus 18.

In operation, ophthalmic instrument 10 is generally positioned relative to the eye to be measured. Container 12 enclosing the optical system is raised or lowered relative to base 16 for proper alignment with the eye being measured. Electrical switch 44 on control apparatus 20 is depressed to activate solenoid 32, which draws core 34 into solenoid 32 for disengaging sides 40 from clamping members 42. This permits relative movement between the first and second plates and pivotal movement of movable support 14 around axis 22 for alignment of the optical system of the ophthalmic instrument relative to the eye being measured.

What is claimed is:

1. An ophthalmic instrument support apparatus, comprising:
    container means for enclosing a portion of the ophthalmic instrument;

a base;

movable support means for pivotally moving said container means relative to said base;

braking means for selectively permitting pivotal movement of said fixed support means relative to said movable support means, having alternatively disposed first and second series of plates, a solenoid with a movable core, a Vee-shaped member attached to the core with the sides of the member extending over the alternatively disposed first and second series of plates, and a clamp member attached to the outermost series of plates and between the sides of the Vee-shaped member; and control means for activating and inactivating the solenoid to permit arcuate movement of said container means.

2. The instrument of claim 1, wherein said braking means having a spring member biasing the Vee-shaped member into clamping position when the control means is inactive.

3. The instrument of claim 1, wherein said movable support means has a pivotal axis and the second series of plates of said braking means are disposed in an arc having a radius drawin from the pivotal axis.

* * * * *